(12) United States Patent
Quijano et al.

(10) Patent No.: US 7,432,241 B1
(45) Date of Patent: Oct. 7, 2008

(54) DEVICE FOR TREATING DIABETES AND METHODS THEREOF

(75) Inventors: Rodolfo C. Quijano, Laguna Hills, CA (US); Hosheng Tu, Newport Beach, CA (US)

(73) Assignee: Onita Inc, Laguna Hills, CA (US)

( * ) Notice: Subject to any disclaimer, the term of this patent is extended or adjusted under 35 U.S.C. 154(b) by 243 days.

(21) Appl. No.: 11/451,552

(22) Filed: Jun. 12, 2006

Related U.S. Application Data

(63) Continuation of application No. 10/320,788, filed on Dec. 16, 2002, now Pat. No. 7,060,684.

(51) Int. Cl.
*A61K 38/00* (2006.01)
*A61K 35/44* (2006.01)

(52) U.S. Cl. .............................. 514/2; 514/21; 424/423

(58) Field of Classification Search ........................ None
See application file for complete search history.

(56) References Cited

U.S. PATENT DOCUMENTS

| 6,387,663 | B1 | 5/2002 | Hall et al. |
| 6,391,052 | B2 | 5/2002 | Buirge et al. |
| 6,395,023 | B1 | 5/2002 | Summers |
| 6,451,047 | B2 | 9/2002 | McCrea et al. |
| 6,752,826 | B2 | 6/2004 | Holloway et al. |
| 7,000,305 | B2 | 2/2006 | Jayaraman |
| 7,037,332 | B2 | 5/2006 | Kutryk et al. |

*Primary Examiner*—Robert Landsman
*Assistant Examiner*—Gyan Chandra

(57) ABSTRACT

A composite supported vascular graft comprising Vascular Endothelial Growth Factor (VEGF) and/or Platelet Derived Growth Factor (PDGF) for enhanced site-specific angiogenesis and methods thereof are disclosed. At least one VEGF, PDGF or angiogenesis factor is incorporated into the composite vascular graft to facilitate enhanced angiogenesis so as the cells are stimulated to migrate to environments having higher concentration of growth factors and start mitosis.

20 Claims, 8 Drawing Sheets

DEVICE FOR TREATING DIABETES AND METHODS THEREOF

CROSS-REFERENCE TO RELATED APPLICATIONS

This application is a continuation application of U.S. patent application Ser. No. 10/320,788, filed Dec. 16, 2002, now U.S. Pat. No. 7,060,684, the entire contents of which are incorporated herein by reference.

FIELD OF THE INVENTION

The present invention relates generally to improved medical device and methods for using same. More particularly, the present invention relates to a vascular graft implant comprising vascular endothelial growth factor (VEGF) and/or platelet derived growth factor (PDGF) for enhanced site-specific angiogenesis and methods thereof.

BACKGROUND OF THE INVENTION

The basic function of an arterial blood vessel is for transportation of blood from the heart to organs and tissues of the body. When a blood vessel is diseased or becomes dysfunctional, a vascular graft is usually employed for implantation to replace or bypass the diseased or dysfunctional blood vessel. The vascular grafts include autologous blood vessel, homograft, cryo-preserved blood vessel, grafts made of synthetic material such as expanded polytetrafluoroethylene (e-PTFE) or polyester (trade name Dacron), and grafts made of biological material, such as bovine internal mammal artery, human umbilical vein, or pericardium.

A special sub-group that has dysfunctional blood vessels belongs to diabetic patients. Diabetes mellitus is characterized by a broad array of physiologic and anatomic abnormalities, for example, altered glucose disposition, hypertension, retinopathy, abnormal platelet activity, aberrations involving medium and small sized vessels, and other problems. Diabetics may depend on insulin for the prevention of ketoacidosis. Developed atrophic ulcer and infected alterations of the foot as a result of complications of diabetes mellitus may require foot amputation. The current treatment may include drug therapy, for example, U.S. Pat. No. 5,871,769 to Fleming et al. discloses methods for the prevention and/or treatment of diabetes mellitus using magnesium gluconate. However, a biocompatible vascular graft may be implanted to enhance blood circulation and eventually to salvage extremity. A vascular graft having enhanced angiogenesis capability or having angiogenesis factors may promote peripheral revascularization or neovascularization for blood perfusion so as to save the diseased foot from amputation. The process of angiogenesis (new capillary formation) is stimulated by angiogenesis factors.

The vascular graft or prosthesis made of synthetic materials is usually porous, compliant, strong, and biocompatible. The micropores of a synthetic prosthesis are believed to facilitate tissue/cells ingrowth from the host so as to accelerate the healing process. It is also suggested that the host cells tend to encapsulate a foreign substrate if the host tissue does not achieve cell infiltration into the substrate. In clinical practices, partially clotted blood, collagen, gelatin or other gelatinous material may be coated upon/into the micropores so that blood leakage during the initial phase of implantation is minimized or for future drug release purposes. U.S. Pat. No. 5,851,230 discloses a vascular graft with a heparin-containing collagen sealant, U.S. Pat. No. 6,352,710 discloses a polymerizable sealant coating that is biocompatible, tissue compliant and drug-loadable; U.S. Pat. No. 6,395,023 discloses a prosthesis coated with a biodegradable, resorbable and biocompatible surface coating embedded with biologically active agents; all three cited patents are incorporated herein by reference.

Jayaraman et al. in U.S. Pat. Appl. Publication 2002/0065552, the entire contents of which are incorporated herein by reference, discloses coating a vascular graft with a nonporous coating to prevent short and long term fluid leakage through the pores of the vascular graft, particularly the coating being polyurethane. The Jayaraman patent is distinguishable with a proprietary Thoralon® polyether urethane urea polyurethane polymer as the coating material.

The vascular prosthesis made of biological material contains collagen as its major component. A biological prosthesis is usually crosslinked to reduce the antigenicity, enhance its antithrombogenicity, and/or improve the durability. Typical crosslinking agents include glutaraldehyde, formalin, dialdehyde starch, polyepoxy compounds or the like. For example, U.S. Pat. No. 4,082,507 discloses a treatment method with glutaraldehyde, dialdehyde starch and formalin. U.S. Pat. No. 4,806,595 discloses a treatment method with polyepoxy compounds and/or heparin. The implantation with a polyepoxy compounds treated graft usually exhibit some tissue regeneration and capillary proliferation, and may account for some degree of angiogenesis. Both patents are incorporated herein by reference.

When a vascular graft is placed in a human body, the inner walls of the graft may become lined with endothelial cells, which possess antithrombotic properties for preventing blood clotting and deposition of blood thrombus on the inner walls. In actual clinical situations, however, lining by the endothelial cells is usually much delayed, and in most cases, only the area of the anastomosis of the vascular graft becomes covered with endothelial cells while remote locations away from the anastomoses are not covered. Accordingly, thrombus continues to deposit on the inner walls where endothelialization is void. Though endothelial seeding or sodding method has been recently developed to assist the endothelialization process, the seeded/sodded cells may separate from the inner wall of a vascular graft and be washed away by the blood stream. For example, U.S. Pat. No. 4,820,626 discloses a method of treating a synthetic or naturally occurring surface with microvascular endothelial cells. One of the major drawbacks is the extra step of collecting autologous endothelial cells, enzymatic digestion by collagenase, centrifugal filtration, and seeding prior to implantation of the graft.

Furthermore, U.S. Pat. No. 5,785,965 discloses a process for sodding modified cells onto a vascular prosthesis for implantation, wherein endothelial cells derived from subcutaneous adipose tissue are genetically modified to express the endothelial cell specific angiogenic factor VEGF. The method accelerates endothelialization on the luminal surface of the vessel. However, during the early stage of transplantation, the sodded cells may separate from the inner wall of a vascular graft and be washed away by the blood stream. It was reported that when endothelial seeding is applied to grafts installed in the canine infrarenal aorta, surface thromboresistance improves significantly over controls only after the seeded grafts have healed for approximately 4 weeks. In the above discussed endothelialization processes, only autologous endothelial cells may be used because of concerns on immunological response. In almost any cell transplantation procedure, immunological response is always a concern.

Noishiki et al. in U.S. Pat. No. 5,387,236 discloses a vascular prosthesis by depositing fragments of biological tissues such as vascular tissues, connective tissues, fat tissues and muscular tissues, and cells such as vascular endothelial cells, smooth muscle cells and fibroblast cells within the wall from the inner side of a vascular prosthesis. Though the patent discloses a method for effectively depositing cells/tissues into the interstices of a vascular prosthesis mostly at adjacent the inner wall, Noishiki et al. does not disclose a method of incorporating vascular endothelial growth factor or platelet derived growth factor to promote angiogenesis and to facilitate in situ proliferation of endothelial cells and/or neovascularization inside the walls of an implanted vascular prosthesis.

Further, Noishiki in U.S. Pat. No. 5,986,168, the entire contents of which are incorporated herein by reference, discloses coating basic fibroblasts growth factor (bFGF), vascular endothelial growth factor (VEGF), platelet-derived endothelial cell growth factor (PDGF), and Hepatocyte growth factor (HGF) to the inner wall of a vascular prosthesis, which is less effective for releasing the growth factors to the surrounding tissue for angiogenesis.

The angiogenesis process is believed to begin with the degradation of the basement members by proteases secreted from endothelial cells activated by mitogens such as vascular endothelial growth factor and basic fibroblast growth factor (bFGF). The cells migrate and proliferate, leading to the formation of solid endothelial cell sprouts into the stromal space, then, vascular loops are formed and capillary tubes develop with formation of tight junctions and deposition of new basement membrane. Recent studies have applied vascular endothelial growth factor to expedite and/or augment collateral artery development in animal models of myocardial and hindlimb ischemia.

Vascular endothelial growth factor (VEGF) is mitogenic for vascular endothelial cells and consequently is useful in promoting neovascularization (angiogenesis) and reendothelialization. Angiogenesis means the growth of new capillary blood vessels. Angiogenesis is a multi-step process involving capillary endothelial cell proliferation, migration and tissue penetration. VEGF is a growth factor having a cell-specific mitogenic activity. It would be desirable to employ a wound healing substrate incorporating a mitogenic factor having mitogenic activity that is highly specific for vascular endothelial cells following vascular graft surgery, balloon angioplasty and/or to promote collateral circulation. U.S. Pat. No. 5,194,596 discloses a method for producing VEGF while U.S. Pat. No. 6,040,157 discloses a specific VEGF-2 polypeptide. Both patents are incorporated herein by reference.

U.S. Pat. No. 5,980,887 to Isner et al. discloses a method to isolate EC (endothelial cell) progenitor from circulating blood and methods for enhancing angiogenesis with endothelial progenitor cells in a patient by administering to the patient an effective amount of an isolated endothelial progenitor cell, wherein the endothelial progenitor cell may include $CD34^+$, $flk-1^-$ or $tie-1^+$. However, Isner et al. in U.S. Pat. No. 5,980,887 does not disclose incorporating VEGF or EC progenitors onto a medical prosthesis for localized site-specific angiogenesis enhancement.

Hammond et al. in U.S. Pat. No. 5,880,090 discloses methods for enhancing the endothelialization of synthetic vascular grafts by administering to a graft recipient an agent that mobilizes bone marrow derived $CD34^+$ cells into the blood stream that enhances the adherence to graft surfaces of blood-borne endothelial progenitors. Again, immunological response to any cell transplantation is generally a clinical concern and Hammond '090 patent does not disclose incorporating EC progenitors onto a medical prosthesis for localized site-specific angiogenesis enhancement.

Gordinier et al. in U.S. Pat. No. 5,599,558 discloses a method of making a platelet releasate product and methods of treating tissues with the platelet releasate. Platelet derived growth factor (PDGF) is a well-characterized dimeric glycoprotein with mitogenic and chemoattractant activity for fibroblasts, smooth muscle cells and glial cells. In the presence of PDGF, fibroblasts move into the area of tissue needing repair and are stimulated to divide in the lesion space itself. It has been reported that the cells exposed to lower PDGF concentrations are stimulated to move to environments having higher concentrations of PDGF and divide. The Gordinier et al. '558 patent is incorporated hereby by reference.

Uncontrolled over-angiogenesis or inappropriate angiogenesis is detrimental to a patient. This inappropriate angiogenesis is mostly related to non site-specific process and may result in proliferation of tumors and/or cancers. For example, it is only after many solid tumors are vascularized as a result of angiogenesis that the tumors begin to grow rapidly and metastasize. Because angiogenesis is so critical to these functions, it must be carefully regulated at any specific site or locality in order to maintain health. In some aspect of the present invention, it is provided a method for treating tumor/cancer or retinopathy with a composite implant having a site-specific angiogenesis antagonist.

A site-specific angiogenesis by incorporating VEGF, PDGF or other growth factors onto a medical material, particularly a cardiovascular device, may attract the progenitor cells, endothelial cells or the like from the circulating blood via a vascular graft to deposit onto the device surface and enhance the needed site-specific angiogenesis at the lesion site. Therefore, there is an urgent clinical need for a vascular graft having incorporated VEGF, PDGF, and the like onto the graft that may provide angiogenesis factors and circulating blood so as to enhance site-specific neovascularization and angiogenesis at the graft and its proximity to treat diabetic foot or ischemia diseases. It is another aspect of the present invention to provide an angiogenesis antagonist for inhibiting undesired angiogenesis.

SUMMARY OF THE INVENTION

In general, it is an object of the present invention to provide a method for preparing a vascular graft having site-specific angiogenesis factor, preferably by incorporating vascular endothelial growth factor and/or platelet derived growth factor onto the vascular graft or other implants at adjacent the tissue contact site. The vascular graft of the present invention may be used to bypass, replace or repair a part of the diseased/dysfunctional blood vessel. It is a further object of the present invention to provide a vascular graft having site-specific angiogenesis factors comprising incorporating at least one vascular endothelial growth factor, or at least one platelet derived growth factor, or other angiogenesis factor, and combination thereof onto the medical device.

In some aspect of the present invention, it is to provide an angiogenesis antagonist to an implant for inhibiting undesired angiogenesis site-specifically, such as tumor, cancer, retinopathy, or the like.

In one preferred embodiment, the vascular graft having site-specific angiogenesis factor comprises at least one vascular endothelial growth factor. Vascular endothelial growth factor, which is also known as vascular permeability factor, is a secreted angiogenic mitogen whose target cell specificity appears to be restricted to vascular endothelial cells. The "angiogenesis factor" of the present invention refers to any compound, substrate, material, specie, factor, or element that stimulates or promotes angiogenesis activity. The angiogenesis factor may comprise one of the following: vascular endothelial growth factor, platelet derived growth factor, tissue treatment factor, and the like. The "vascular endothelial growth factor" in this invention refers broadly to any and all the members of the vascular endothelial growth factor family, which may comprise polynucleotides, polypeptides encoded by such polynucleotides that facilitate angiogenesis, and the like. U.S. Pat. No. 6,040,157 to Hu et al. discloses general characteristics and specific properties of vascular endothelial growth factor and is incorporated herein by reference. VEGF has at least four different forms of 121, 165, 189 and 206 amino acids due to alternative splicing, which are designated as VEGF121, VEGF165, VEGF189, and VEGF206, respectively.

In one aspect, VEGF121 and VEGF165 are soluble that can be incorporated onto the vascular graft of the present invention. In one embodiment, VEGF121, VEGF165, VEGF189, VEGF206 or other angiogenesis factors are mixed with a substrate, such as collagen, heparinized collagen, crosslinked collagen, crosslinked heparinized collagen, blood clot, drug, hydrogel, protein, or the like, prior to be incorporated onto the vascular graft, preferably from outer wall of the graft. In another embodiment, the method for incorporating the vascular endothelial growth factors comprises a step of impregnating the growth factors onto the vascular graft. In a further preferred embodiment, the step further comprises applying pressure to force impregnating the vascular endothelial growth factors into the vascular graft, preferably from the outer side or the tissue-contacting side of the vascular graft.

In some aspect, VEGF189 and VEGF206 are bound to heparin containing proteoglycans in the cell surface. Therefore, a heparinized medical material, such as the one disclosed by Noishiki et al. (U.S. Pat. Nos. 4,806,595, 5,387,236, and 5,986,168), has the capability of incorporating the desired vascular endothelial growth factor by binding VEGF189 and/or VEGF206 for site-specific angiogenesis. All three Noishiki et al. patents are included herein by reference in their entirety. The vascular endothelial growth factor of the present invention may be selected from the group consisting of VEGF, VEGF-2, bFGF, VEGF121, VEGF165, VEGF189, VEGF206, and the like.

The "platelet derived growth factor" in this invention may cover broadly PDAF (platelet derived angiogenesis factor), PDGF (platelet derived growth factor), TGF-β (transforming growth factor beta), PDEGF (platelet derived epidermal growth factor), PDWHF (platelet derived wound healing formula), and the like. The platelet derived growth factor of the present invention may also comprise any substrate that contains at least one of the above-referred PDAF, PDGF, TGF-β, PDEGF, or PDWHF that possess angiogenesis activity, wherein said substrate may comprise blood clot or blood components. U.S. Pat. No. 5,599,558 to Gordinier et al. discloses general properties and constituents of platelet derived growth factor, the entire contents of the Gordinier et al. '558 patent is incorporated herein by reference.

The "tissue treatment factor" in this invention may refer to any chemical, substrate, material, and solution that could treat a tissue to render the tissue more angiogenic or have more angiogenesis propensity. A tissue treated by a polyepoxy compound or combinations of polyepoxy compounds, as disclosed in U.S. Pat. No. 4,806,595, the entire contents of which is incorporated herein by reference, may have some angiogenesibility. A vascular graft incorporating tissue treatment factor could render the medical device with enhanced angiogenesis.

In accordance with the preferred embodiment of the present invention, the vascular graft may be selected from the group consisting of autologous graft, homograft, biological graft, synthetic graft, composite graft, supported graft, or the like. Furthermore, the biological graft or tubular conduit is selected from the group consisting of internal mammary artery, umbilical vein, urethra, pericardium, jugular vein, genetically altered blood vessel, and combinations thereof. The vascular graft may be either heparinized or crosslinked, wherein an agent for crosslinking the vascular graft may be selected from the group consisting of glutaraldehyde, formalin, dialdehyde starch, polyepoxy compounds, and the like. The vascular graft of the present invention comprises site-specific angiogenesis factor adapted for enhancing angiogenesis.

In one aspect, a supported vascular graft of the present invention may be externally supported or internally supported, wherein the support element may be expandably collapsible suitable for delivery by a percutaneous catheter or cannula. In some aspect, the vascular graft is an expanded polytetrafluoroethylene tubular conduit. In another aspect, the supported vascular graft may comprise a support element or structure with an external cover, jacket or encapsulator. In one embodiment of the present invention, it is provided a composite vascular graft having a site-specific angiogenesis factor for enhanced angiogenesis comprising: a supported vascular graft; and a substrate coated onto the vascular graft, wherein the substrate is selected from the group consisting of collagen, heparinized collagen, crosslinked collagen, and crosslinked heparinized collagen, and wherein the substrate is incorporated with the angiogenesis factor. In a preferred embodiment, it is provided a composite vascular graft having a site-specific angiogenesis factor for enhanced angiogenesis comprising: a supported vascular graft; and a tubular conduit wrapped onto the vascular graft, wherein the tubular conduit is incorporated with an angiogenesis factor.

In another preferred embodiment, a method for treating diabetic foot of a patient comprising implanting percutaneously a composite vascular graft for enhancing blood perfusion, wherein the composite vascular graft comprises site-specific angiogenesis factors. The angiogenesis factor may be selected from the group consisting of VEGF, VEGF-2, aFGF, bFGF VEGF121, VEGF165, VEGF189, VEGF206, PDGF, PDAF, TGF-β, PDEGF, PDWHF, polyepoxy compounds, and combination thereof.

Furthermore, a process for implanting a vascular graft or a composite supported vascular graft having site-specific angiogenesis factor comprises (a) percutaneously inserting the composite supported vascular graft at its expandably collapsible state within a delivery apparatus to the implantation site; (b) positioning the delivery apparatus having the composite supported vascular graft at the desired implantation site; and (c) implanting the composite vascular graft by releasing the composite vascular graft from the delivery apparatus and securing the graft after expanding the support element of the supported graft. After the graft is in place, the endothelial cells and cells progenitors deposit site-specifically on the device for expedited angiogenesis and mitosis. The vascular graft for the implantation process may comprise at least one vascular endothelial growth factor or platelet derived growth factor, wherein the vascular graft may be selected from the group consisting of autologous graft, homograft, biological graft, synthetic graft, composite vascular graft, and supported vascular graft.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

The preferred embodiments of the present invention described below relate particularly to a composite vascular graft having a site-specific angiogenesis factor for enhanced angiogenesis comprising a supported vascular graft and a substrate coated onto the supported vascular graft, wherein the substrate is incorporated with the angiogenesis factor. While the description sets forth various embodiment specific details, it will be appreciated that the description is illustrative only and should not to be construed in any way as limiting the invention. Furthermore, various applications of the invention, and modifications thereto, which may occur to those who are skilled in the art, are also encompassed by the general concepts described below.

Referring to FIGS. 1 to 8, what is shown is an embodiment of a vascular graft having site-specific angiogenesis factor comprising at least one factor of the following: vascular endothelial growth factor, platelet derived growth factor, tissue treatment factor, or combination thereof. In one aspect, a supported vascular graft of the present invention may be externally supported or internally supported, wherein the support element or structure may be expandably collapsible. In another aspect, the supported vascular graft may comprise a support element or structure with an external cover, jacket or encapsulator functioning as an implantable vascular graft. The "composite vascular graft" is intended herein to mean a regular vascular graft or a supported vascular graft that comprises at least one angiogenesis factor at adjacent its exterior wall or a majority of the at least one angiogenesis factor loaded close to the exterior surface of the graft.

In some aspect, the support element or structure, such as an expandably collapsible end retaining-element, of a supported vascular graft of the present invention is to facilitate percutaneously implantation by inserting the supported vascular graft with collapsed end retaining-elements within the lumen of a delivery apparatus. At an appropriate implantation site, the supported vascular graft with the collapsed end retaining-elements is released from the delivery apparatus. The collapsed end retaining-elements are thereafter expanded to stabilize the graft in place. The step of expanding the end retaining-elements may be carried out by an inflatable balloon, an expandable basket, or the like. In another aspect, the end retaining-element may be a self-expandable element made of spring steel. In still another aspect, the end retaining-element may be made of a temperature-actuated shape memory material, such as a shape memory Nitinol. The step of expanding the end retaining-element may be carried out by heating (for example, radiofrequency heating or hot saline heating) or cooling the temperature-actuated shape memory end element above or below its shape-transitional temperature.

Figure 1:
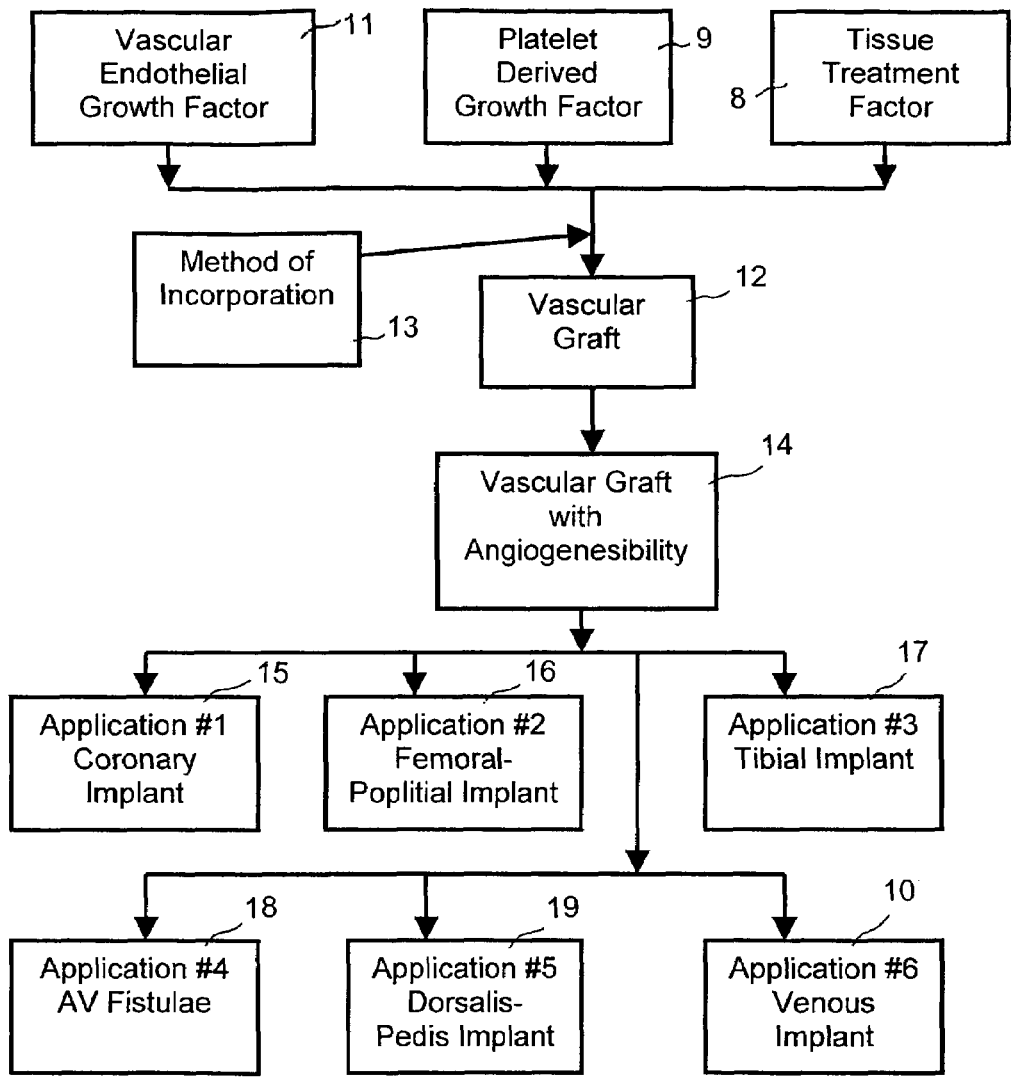
FIG. 1 is a schematic diagram illustrating the steps of preparing a vascular graft with angiogenesibility in accordance to the principles of the present invention.

FIG. 1 shows a schematic diagram illustrating the steps of preparing a vascular graft with angiogenesibility in accordance to the principles of the present invention. A vascular graft is a biocompatible material that may be used to fill, fix, replace, substitute, treat, or repair a part of the diseased/dysfunctional blood vessels, wherein a supported vascular graft is the vascular graft with a support element(s) secured to the graft to extend the graft outwardly radially. In one embodiment, the vascular graft or supported vascular graft comprises site-specific angiogenesis factor adapted for enhancing angiogenesis (that is, a composite supported vascular graft). In one preferred embodiment, the angiogenesis factor may be a polyepoxy compound or combination of polyepoxy compounds. In another embodiment, the angiogenesis factor may be selected from the group consisting of VEGF, VEGF-2, bFGF (basic fibroblast growth factor), aFGF (acidic fibroblast growth factor), VEGF121, VEGF165, VEGF189, VEGF206, PDGF (platelet derived growth factor), PDAF, TGF-α (transforming growth factor-alpha), TGF-β (transforming growth factor-beta), PDEGF, PDWHF, and combination thereof. In a further embodiment, the vascular graft is selected from the group consisting of autologous graft, homograft, biological graft, synthetic graft, supported graft, and the like.

Angiogenesis factors include growth factors in general, wherein the growth factors can be defined as multifunctional, locally acting, intercellular signaling polypeptides which control both the ontogeny and maintenance of tissue form and function. Growth factors that can be used in the invention further include epidermal growth factor (EGF), and colony stimulating factor (CSF). New factors are continually discovered and new functions are continually reported; they become available commercially. In one aspect, preferred growth factors are basic fibroblasts growth factor (bFGF), vascular endothelial growth factor (VEGF), platelet-derived endothelial cell growth factor (PDEGF), and hepatocyte growth factor (HGF). The bFGF is a powerful mitogen for a wide variety of cell types including, fibroblast, neurectodermal cells and capillary and large vessel endothelial cells. VEGF is a mitogen for endothelial cells. PDEGF induces multiplication of fibroblasts and smooth muscle cells. BFGF and VEGF are especially preferred.

Vascular endothelial growth factor is obtained from a quality manufacturer or prepared according to the available techniques/protocols in the art. At least one vascular endothelial growth factor 11 is incorporated onto the vascular graft 12 by a method of incorporation 13. Other angiogenesis factor, such as platelet derived growth factor 9 or tissue treatment factor 10 may also be used in the present invention. In one embodiment, the method of incorporation may comprise mixing, suspending, or dispersing the angiogenesis factor with a substrate, such as collagen, heparinized collagen, crosslinked collagen, blood clot, blood, blood component, crosslinked heparinized collagen, drug, drug carrier, protein, hydrogel, tubular conduit, their mixture, and the like. In another embodiment, the method of incorporation may comprise encapsulation of the angiogenesis factor as a drug or drug carrier. In still another embodiment, the method of incorporation may comprise impregnating, immersing, soaking, spraying, pressure impregnating, entrapping the angiogenesis factor into the vascular graft from within the lumen or from the outer periphery of the graft. The vascular graft or the vascular graft having support elements with angiogenesibility 14 may be used as a vascular graft in various procedures such as coronary implant 15, femoral-poplitial implant 16, tibial implant 17, AV fistulae 18, dorsalis-pedis implant 19 or venous implant 10.

Collagen is a protein which is highly compatible with cells. Collagen used and defined in the present invention may comprise a soluble collagen, an insoluble collagen, a chemically modified collagen, a collagen derivative such as gelatin, a polypeptide obtained by hydrolysis of collagen, and a natural collagen present in natural tissues.

Schwartz in U.S. Pat. No. 6,080,190, the entire contents of which are incorporated herein by reference, discloses an intraluminal stent comprising fibrin onto the stent that attracts plasminogen in a circulating plasma protein, the adsorbed plasminogen being converted to plasmin by plasminogen activator released from the vascular endothelium, wherein the plasmin then breaks down the fibrin into collection of soluble peptide fragments. Schwartz in '190 patent further discloses included with the fibrin a therapeutic substance of anticoagulant drugs, antiplatelet drugs, antimetabolite drugs and antimitotic drugs.

Buirge et al. in U.S. Pat. No. 6,391,052, the entire contents of which are incorporated herein by reference, discloses a stent with collagen coating on metal stent surface via electrodepositing, the collagen including a drug or other agent such as heparin for release after stent deployment. However, neither angiogenesis factor within the collagen nor collagen within micropores of a composite vascular graft is disclosed.

Anderson et al. in U.S. Pat. No. 6,328,762, the entire contents of which are incorporated herein by reference, discloses a porous vascular graft implant with adherent cells adhered to the outer surface of the implant, the adherent cells being transfected with at least one recombinant nucleic acid molecule encoding a protein that enhances patency of the graft implant. However, neither a supported vascular graft nor collagen within pores of a composite supported vascular graft as a substrate carrier is disclosed.

Figure 2:
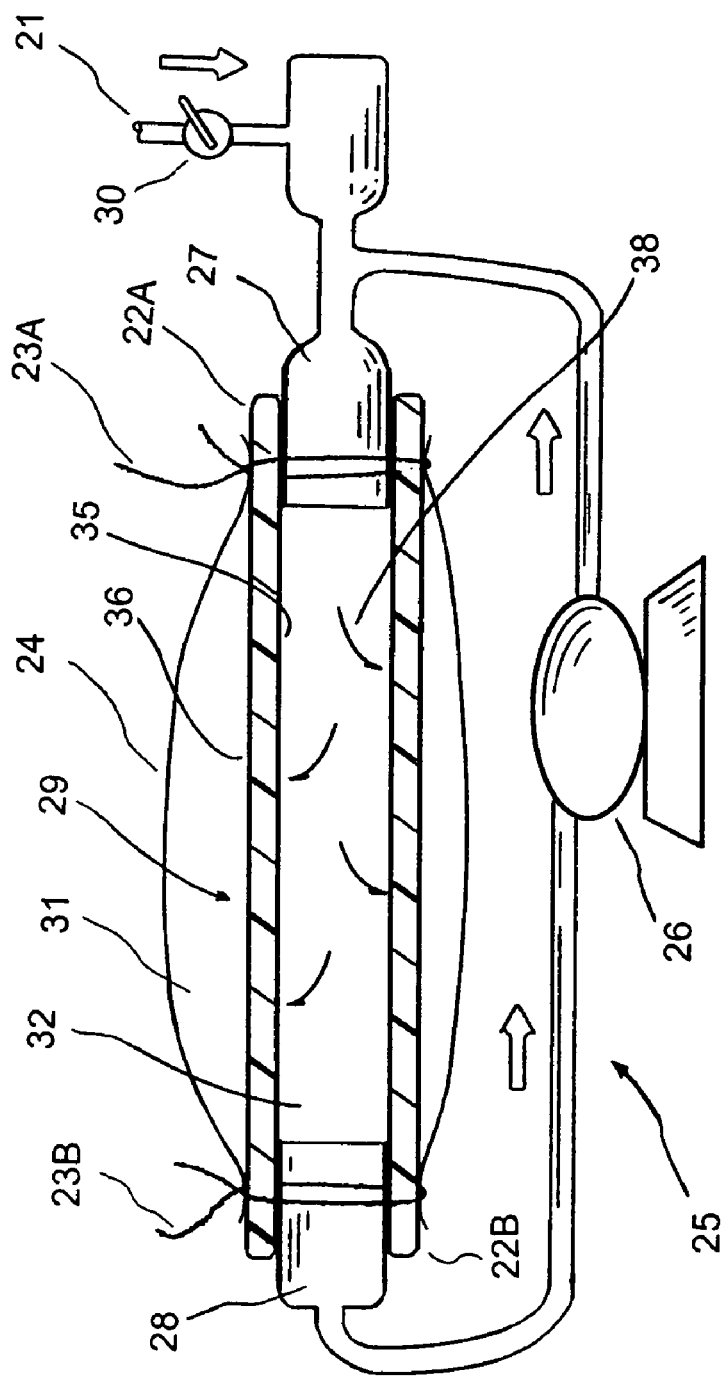
FIG. 2 is one embodiment of the process for preparing a vascular graft having angiogenesis factor at the inner wall of the vascular graft.

FIG. 2 shows one embodiment of the process for preparing a vascular graft having angiogenesis factor at the inner wall of the vascular graft. A vascular graft 29 comprises two end sections 22A, 22B, an inner wall 35, an outer surface 36 and a lumen 32. One end section 22A of the vascular graft 29 is wrapped around and over an inlet section 27 of a circulating impregnating system 25 tightly by a ligature 23A. Similarly, the other end section 22B of the vascular graft 29 is wrapped around and over an outlet section 28 of the circulating impregnating system 25 tightly by another ligature 23B. For a preferred impregnating method, a non-permeable radially expanded tubular arrangement 24 may optionally be used to facilitate a desired differential pressure across the wall of the vascular graft 29 between the lumen 32 and the outer space 31. The outer space 31 between the outer surface 36 of the vascular graft 29 and the tubular arrangement 24 can be vacuumed so as to generate the desired differential pressure for a forced impregnation method.

An impregnating medium containing at least one angiogenesis factor is introduced from the inlet port 21 into the circulating impregnating system 25. A pump 26 or the like may be used to circulate the impregnating medium through the lumen 32 of the vascular graft 29 so as to impregnate the angiogenesis factor onto or into the inner wall 35. In an alternate embodiment of forced impregnation method, the impregnating medium is introduced into the inlet port 21 at a pressure and maintained at an elevated pressure in the circulating impregnating system 25 by a control valve 30 next to the medium inlet port 21. The impregnating medium flows radially outwardly 38 from the lumen 32 towards the inner wall 35 of the vascular prosthesis. By doing forced impregnation or facilitated impregnation, the angiogenesis factor is firmly impregnated onto the vascular graft 29. The efficiency and completeness of impregnation may be affected by the flow rate of the circulating impregnating system, the concentration of angiogenesis factor in the impregnating medium, the differential pressure across the wall of the graft, and the characteristics of the angiogenesis factor employed.

Figure 3:
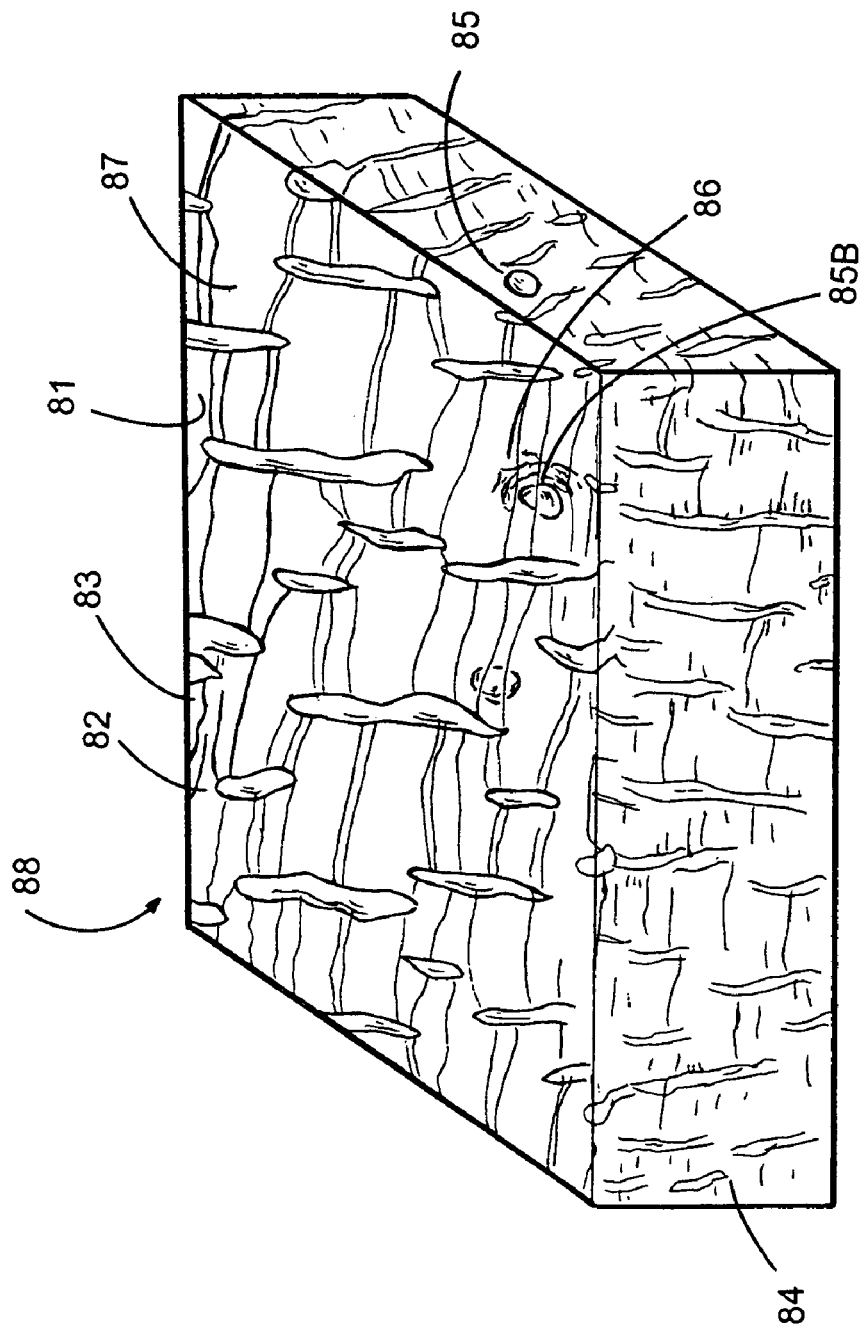
FIG. 3 is a preferred embodiment of the vascular graft incorporating site-specific angiogenesis factors at the outer side of the medical device.

In one aspect, FIG. 3 shows an embodiment of the vascular graft having angiogenesis factors at the outer side and within the matrix of the vascular graft. The vascular graft or tubular conduit of the present invention may comprise a synthetic graft or synthetic tubular conduit made of synthetic material, such as expanded polytetrafluoroethylene (ePTFE) or polyester, a biological material or a blood vessel graft (that is, a biological tubular conduit), such as autologous internal mammary artery, autologous saphenous vein, cryo-preserved allograft, or a supported graft. A biological material of the present invention is usually crosslinked or tanned. A biological material or a biological graft may be crosslinked by glutaraldehyde, dialdehyde starch, formalin, other crosslinking agent, or the like. On the other hand, the biological material of the present invention is not crosslinked. The biological material or vascular graft of the present invention may be heparinized or treated rendering the graft anti-thrombogenic.

Further, it is one aspect of the present invention to provide a composite tubular medical implant for treating esophagus, trachea, colon, biliary tract, or urinary tract having a site-specific angiogenesis factor or antagonist comprising: a supported tubular medical implant; and a substrate coated onto said supported tubular medical implant, wherein said substrate is selected from the group consisting of collagen, heparinized collagen, crosslinked collagen, and crosslinked heparinized collagen, and wherein said substrate is incorporated with said angiogenesis factor or antagonist. The biological tubular conduit may be selected from the group consisting of internal mammary artery, umbilical vein, urethra, pericardium, jugular vein, genetically altered blood vessel, esophagus, trachea, colon, biliary tract, urinary tract, and combinations thereof.

Kerr in U.S. Pat. No. 6,102,918, the entire contents of which are incorporated herein by reference, discloses an instrument for supporting a collapsible low-profile stent-reinforced tubular vascular graft during endovascular implantation. The graft further comprises a self-expanding stent generating a circumferential pressure to hold the graft in place when disposed therein. Neither an angiogenesis factor nor a composite vascular graft is disclosed.

McCrea et al. in U.S. Pat. No. 6,451,047, the entire contents of which are incorporated herein by reference, discloses an elastically self-expanding endoluminal stent partially encapsulated by an encapsulator, that is, a substantially monolithic expanded polytetrafluoroethylene (ePTFE) covering. McCrea et al. patent is distinguishable with an interlayer member of a pair of unsintered ePTFE rings between the abluminal tubular layer of expanded polytetrafluoroethylene and the stent.

Banas et al. in U.S. Pat. No. 6,383,214, the entire contents of which are incorporated herein by reference, discloses a radially expandable vascular stent sandwiched between two encapsulator layers comprised of expanded polytetrafluoroethylene, wherein the stent has a length greater than the length of each of the two encapsulator layers. Banas et al. '214 patent is distinguishable with a sandwiched vascular graft system in absence of collagen coating loaded with angiogenesis factors or angiogenesis antagonists.

Freidberg in U.S. Pat. No. 6,254,627, the entire contents of which are incorporated herein by reference, discloses a jacketed stent assembly, wherein the cylindrical jacket is a biocompatible, non-thrombogenic expandable material of serous pericardium separated from the outer layer of pericardium. The Freidberg '627 patent is further distinguishable with the stent including at least one therapeutic or diagnostic agent releasibly contained in the cylindrical jacket.

Yang et al. in U.S. Pat. No. 6,371,981, the entire contents of which are incorporated herein by reference, discloses a graft system including either a support ring or a support sleeve in providing transitional support to either an end or a side of a graft to a host, wherein the support sleeve surrounds the graft so that the opening of the support sleeve is aligned with the side opening of the graft. Yang et al. '981 patent is distinguishable with a support sleeve on a vascular graft system in absence of collagen coating loaded with angiogenesis factors.

Further, Yang in U.S. Pat. No. 6,379,382, the entire contents of which are incorporated herein by reference, discloses a prosthesis having a cylindrical stent with a two-layer cover provided about the periphery of the stent as a drug reservoir, wherein the two layers of material are stitched to the stent. Yang et al. '382 patent is distinguishable with a two-layer cover stitched to the stent in absence of collagen coating loaded with angiogenesis factors.

As illustrated in FIG. 3, an ePTFE vascular graft comprises an exterior surface or tissue-contacting surface 81 and the interstices or matrix 84. The ePTFE vascular graft 88 comprises nodes 82, fibrils 83, and void 87 in-between the fibrils. The void volume or porosity of an ePTFE vascular graft may be as high as 85% air surrounded by 15% pure expanded PTFE material. Angiogenesis factor 85 is impregnated onto the vascular graft 88 at or close to the exterior surface 81 by a conventional method of incorporation discussed above. In accordance to an alternate embodiment, some of the angiogenesis factors 85B are impregnated onto the vascular graft along with a substrate 86, wherein the substrate may be selected from the group consisting of collagen, heparinized collagen crosslinked collagen, crosslinked heparinized collagen, blood clot, blood, tubular conduit, or the like. In one preferred embodiment, one method to incorporate the angiogenesis factor onto a vascular graft is to incorporate the angiogenesis factor on a tubular conduit, and wrap the tubular conduit onto the vascular graft thereafter to make a composite vascular graft of the present invention. The incorporated angiogenesis factor may also stay inside the interstices 84 not far away from the outer or exterior surface 81. The angiogenesis factor thus has a site-specific therapeutic effect when the vascular graft is implanted.

Figure 4:
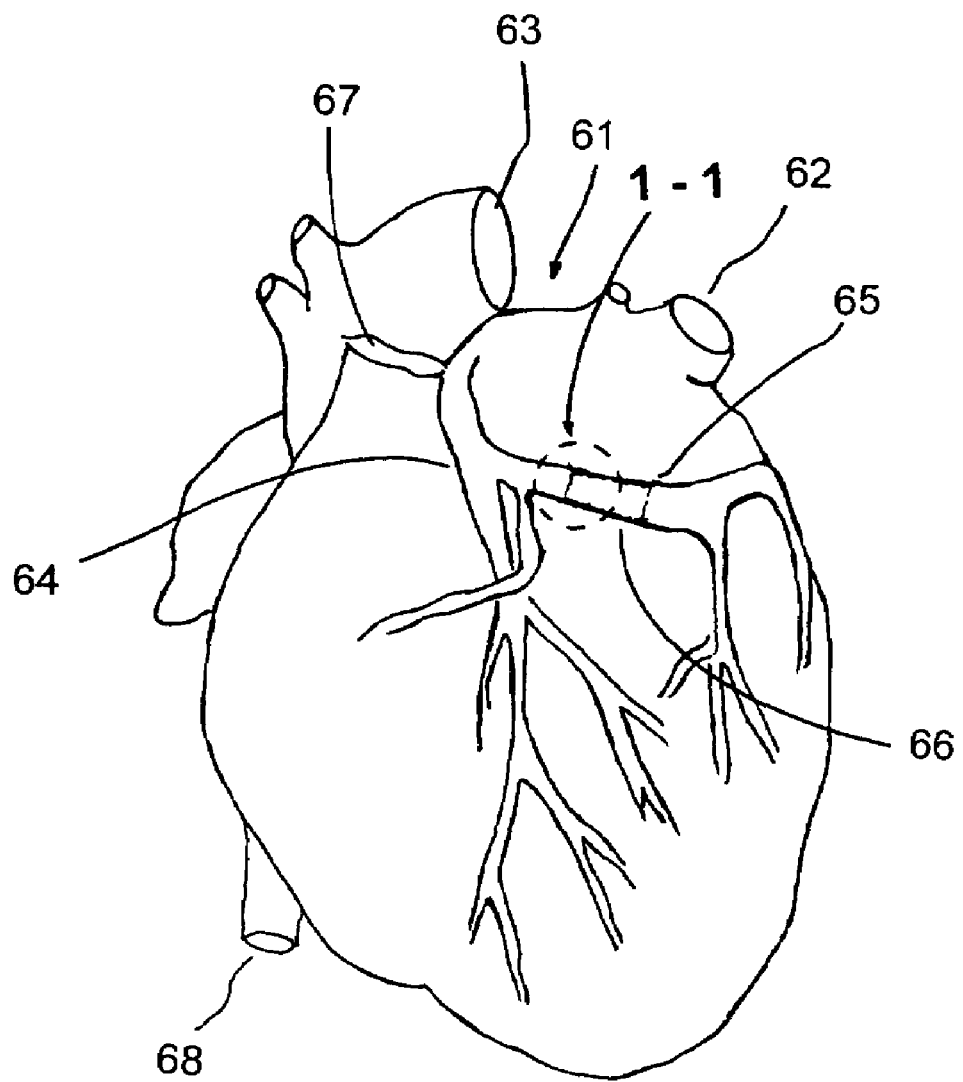
FIG. 4 is a perspective view of a coronary artery bypass grafting using a vascular graft of the present invention.

FIG. 4 shows a perspective view of a coronary artery bypass grafting using a vascular graft of the present invention. The heart 61 includes several vital blood vessels, such as coronary arteries, aorta 63, pulmonary artery 62, superior vena cava 67 and inferior vena cava 68. The coronary artery system includes left anterior descending coronary artery 64, left circumflex coronary artery 66 and coronary vasculature branches. A vascular graft 65 of the present invention is implanted to replace a portion of the diseased/dysfunctional coronary artery. Section 1-1 shows the junction region of the vascular graft 65 and its host coronary artery 66. The graft can also implanted as a bypass or implanted within an artery for releasing angiogenesis factors or antagonists.

Figure 5:
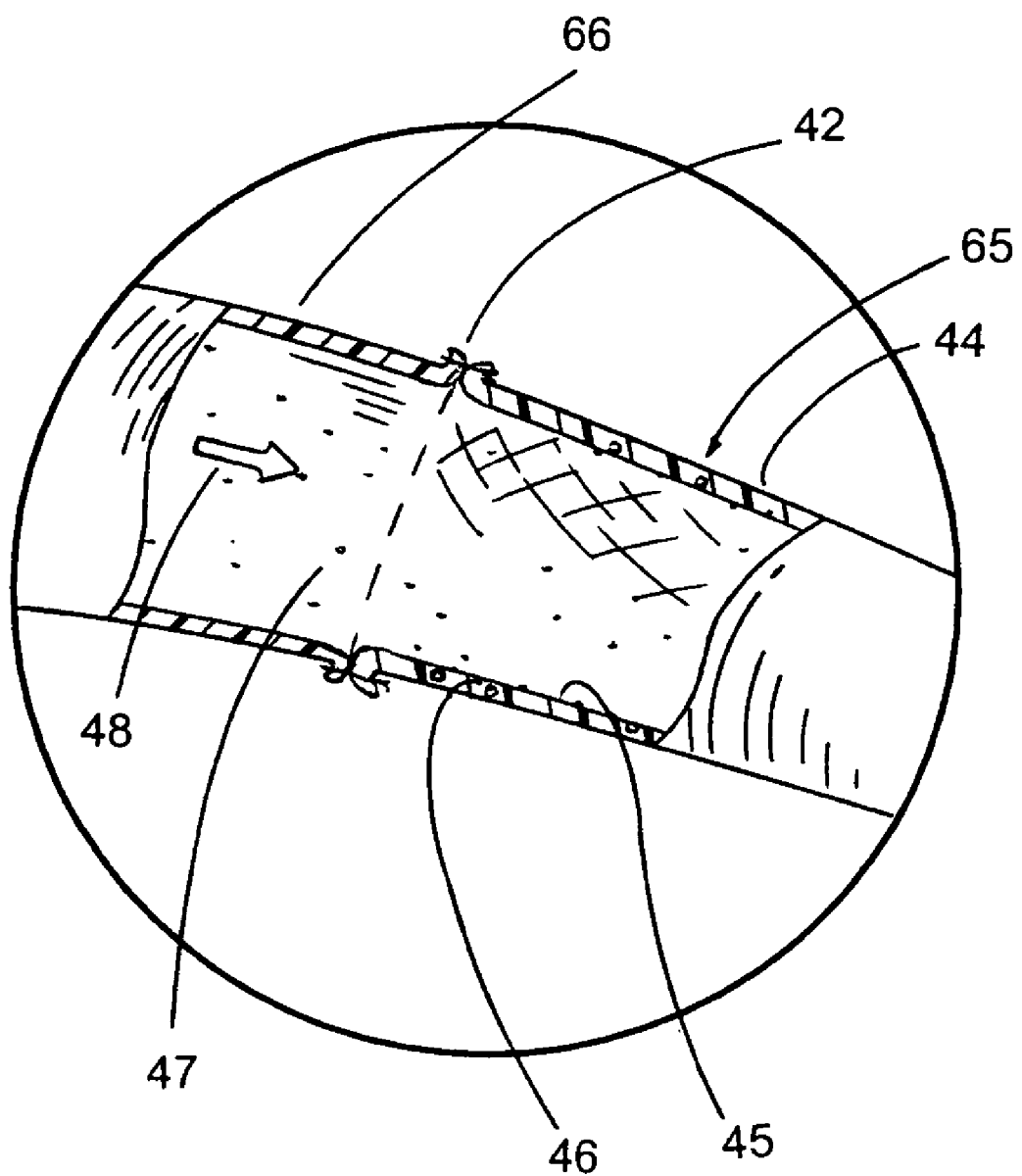
FIG. 5 is an enlarged view of the section 1-1 of FIG. 4, illustrating implantation of a coronary artery bypass graft according to one principle of the present invention.

FIG. 5 shows an enlarged cross-sectional view of the section 1-1 of FIG. 4, illustrating implantation of a coronary artery graft according to the principles of the present invention. The vascular graft 65 is sutured to its host artery 66 at an anastomosis 42. Different modes of suturing techniques may be employed, such as running suture, interrupted suture, stapling or the like. As shown in FIG. 5, blood flow 48 is in the direction from the host artery 66 toward the vascular graft 65. Blood usually contains red blood cells, white blood cells, platelet, proteins, plasma and small quantity of other cells and cells progenitor, such as free flowing endothelial cells 47, stem cells, $CD34^+$, and the like. The vascular graft 65 may comprise an inner wall 45 and an outer wall 44, wherein pre-incorporated angiogenesis factor 46 may stay or be entrapped at adjacent the inner wall 45 or adjacent the outer wall 44. The incorporated angiogenesis factor 46 may promote the desired angiogenesis and/or neovascularization to the surrounding tissue with any attracted endothelial cells inside the wall of the graft 65.

In some aspect of the present invention, it is provided a composite vascular graft having a site-specific angiogenesis factor for enhanced angiogenesis comprising: a supported vascular graft; and a substrate coated onto the supported vascular graft, wherein the substrate is selected from the group consisting of collagen, heparinized collagen, crosslinked collagen, and crosslinked heparinized collagen, and wherein the substrate is incorporated with or loaded with the angiogenesis factor. In a further aspect of the present invention, it is provided that the supported vascular graft has suitable scaffold configured for retaining the substrate or angiogenesis factors or antagonists, wherein the suitable scaffold is formed by an acellular process. In one alternate aspect, the scaffold is one type of vascular grafts of the present invention.

Ragheb et al. in U.S. Pat. No. 6,299,604, the entire contents of which are incorporated herein by reference, discloses a coated implantable device having a coating layer poised on one side of the device and a layer of bioactive material posited over at least a portion of the coating layer adapted for a controlled release of the bioactive material. However, Ragheb et al. device is neither a composite supported vascular graft nor a device with angiogenesis factor incorporated with a substrate coated onto the graft.

Figure 6:
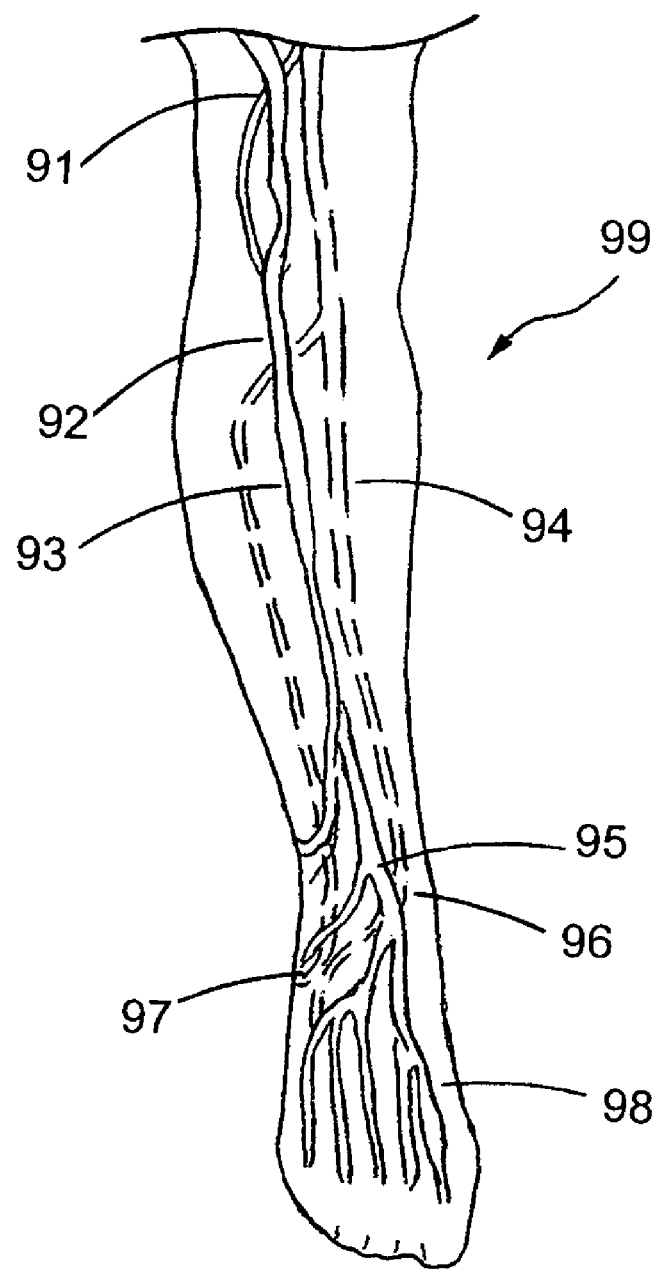
FIG. 6 is a perspective view of the lower extremity of a patient having diseased/dysfunctional arteries available for graft implantation leading to enhanced angiogenesis and diabetic foot treatment.

FIG. 6 shows a perspective view of the lower extremity 99 of a patient having diseased/dysfunctional arteries available for graft implantation leading to enhanced angiogenesis and diabetic foot treatment. The major arteries that may become dysfunctional for a diabetes patient include poplitial artery 91, fibular artery 92, anterior tibial artery 93, posterior tibial artery 94, dorsalis pedis artery 95, medial plantar artery 96, lateral plantar artery 97, digital artery 98, and the like. In one embodiment, a method for treating diabetic foot of a patient comprises implanting a composite vascular graft for enhanced blood perfusion, wherein the composite vascular graft comprises site-specific angiogenesis factors. The composite vascular graft may be implanted for enhanced blood perfusion and angiogenesis in a surgical procedure selected from the group consisting of coronary artery implant, femorofemoral artery implant, femoral-poplitial artery implant, femoro-tibial artery implant, fibular artery implant, tibial artery implant, plantar artery implant, dorsalis-pedis artery implant, AV fistulae, and venous implant, or may be implanted percutaneously.

A process for implanting a vascular graft or a composite vascular graft having site-specific angiogenesis factors comprises the steps of preparing an implantation site, positioning the vascular graft at the implantation site, and implanting the vascular graft. The process may comprise a surgical procedure selected from the group consisting of coronary artery implant, femorofemoral artery implant, femoral-poplitial artery implant, femoro-tibial artery implant, fibular artery implant, tibial artery implant, plantar artery implant, dorsalis-pedis artery implant, AV fistulae, and venous implant.

In another aspect, the process for implanting a vascular graft or a composite vascular graft having site-specific angiogenesis factors comprises the steps of percutaneously inserting the composite vascular graft at its expandably collapsed state within a delivery apparatus to the implantation site, positioning the delivery apparatus having the composite vascular graft at the desired implantation site and implanting the composite vascular graft by releasing the composite vascular graft from the delivery apparatus and deploying the graft. Since the composite vascular graft is to be implanted within a blood vessel or the like, the force to deploy or to expand the supported vascular graft enabling graft placement in place is much lower than that force used in the normal coronary stenting, typically at 12-20 atmospheres. In some aspect of the present invention, it is provided that an expanding force for the end retaining-element is about 0.1 to 2 atmospheres.

In some aspect, the method for treating diabetic foot of a patient comprising implanting percutaneously a composite vascular graft for enhancing blood perfusion, wherein the composite vascular graft comprises site-specific angiogenesis factors. A delivery means for percutaneously delivery and deployment of the composite supported vascular graft of the present invention is well known to an ordinary artisan who is skilled in the art. For example, Trerotola et al. in U.S. Pat. No. 5,755,775, the entire contents of which are incorporated herein by reference, discloses a stent-graft having end members. In some aspect of the present invention, it is provided (FIG. 7A and FIG. 8A) a composite vascular graft comprising a distal end having a distal end element 54, a proximal end having a proximal end element 54, and coupling means 57, 77 for coupling the distal end element and the proximal end element, wherein at least one end element 54 is collapsibly expandable configured to stabilize the graft end section 56 in place after deployment. In one aspect, the collapsible expansion of the end element is a full circumferential expansion (as shown in FIGS. 7B and 8B) while in another aspect, the collapsible expansion is a partial circumferential expansion (not shown).

In some aspect of the present invention, it is provided a composite tubular medical implant for treating vascular vessels, esophagus, trachea, colon, biliary tract, or urinary tract having a site-specific antagonist comprising: a supported tubular medical implant; and a substrate coated onto the exterior wall of the supported tubular medical implant, wherein the substrate is selected from the group consisting of collagen, heparinized collagen, crosslinked collagen, and crosslinked heparinized collagen, and wherein the substrate is incorporated with the angiogenesis antagonist. Lee et al. in U.S. Pat. No. 6,395,548, entire contents of which are incorporated herein by reference, discloses a method of inhibiting angiogenesis by administering a compound which inhibits binding of endothelial PAS (Per-AhR-Arnt-Sim) domain protein-1 to cis-acting transcription regulatory sequence in the promoter region of a gene encoding an angiogenic factor.

Figure 7B:
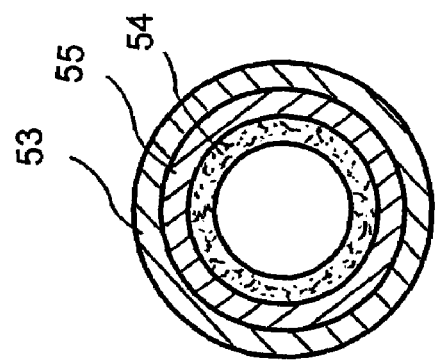
FIG. 7B is an end cross-sectional view of the composite vascular graft in FIG. 7A.
Figure 7A:
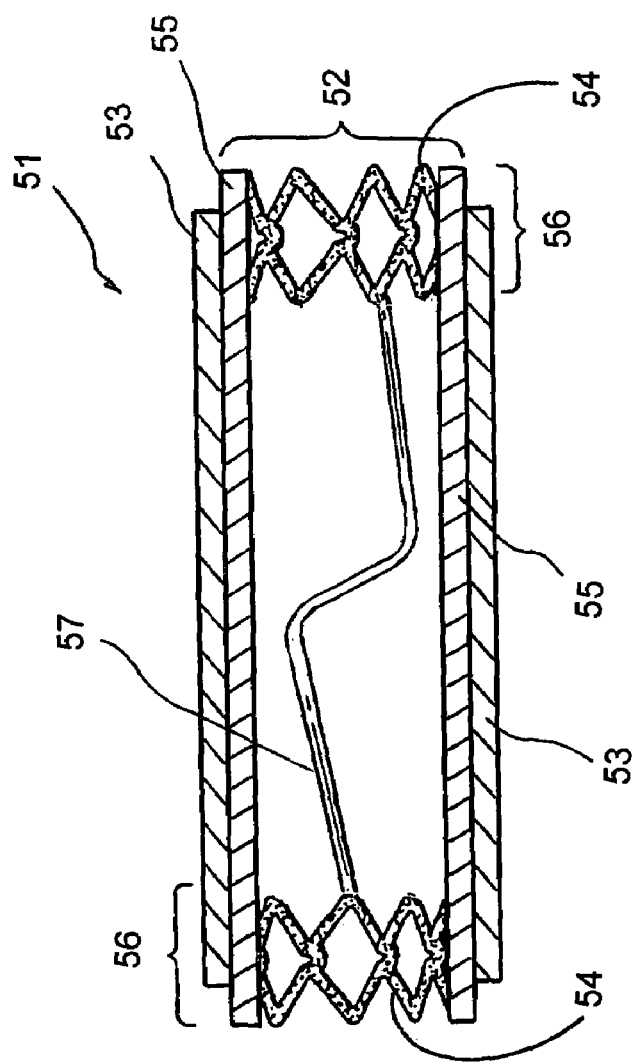
FIG. 7A is an illustrative example of a composite vascular graft with an endoluminal support element and end retaining-elements.

FIG. 7A shows an illustrative example of a composite vascular graft with an endoluminal support element having end retaining-elements, while FIG. 7B shows an end cross-sectional view of the composite vascular graft in FIG. 7A. In one aspect, the composite vascular graft 51 has at least one site-specific angiogenesis factor for enhanced angiogenesis comprising a supported vascular graft 52, and a tubular conduit 53 wrapped onto the supported vascular graft 52, wherein the tubular conduit 53 is incorporated with the at least one angiogenesis factor. The supported graft 52 further comprises two end retaining-elements 54 and an endoluminal support 57 securely coupled to the two end retaining-elements 54, wherein each of the end retaining-elements 54 is secured to one respective end section 56 of the vascular graft 55 by suturing, stitching, welding or gluing techniques. In one aspect, the end retaining-element 54 is an expandable support to radially extend the end section 56 of the vascular graft firmly against the vessel wall of a native blood vessel when implanted percutaneously. The endoluminal support 57 which can be a straight, spiral or curved structure is to secure the two end retaining-elements 54 together at a collapsed state or at an expanded state of the composite supported vascular graft 51. Depending on the clinical needs and configuration, the angiogenesis factor-loaded tubular conduit 53 may have the same or different longitudinal length as the vascular graft 55. Furthermore, the tubular conduit 53 covers fully or at least a portion of the outer surface of the supported vascular graft 52.

Figure 8B:
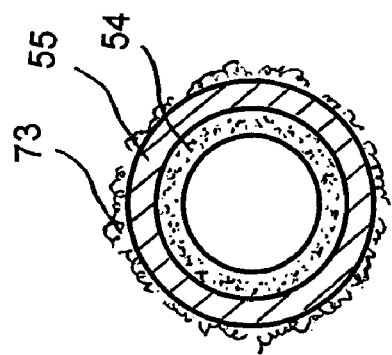
FIG. 8B is an end cross-sectional view of the composite vascular graft in FIG. 8A.
Figure 8A:
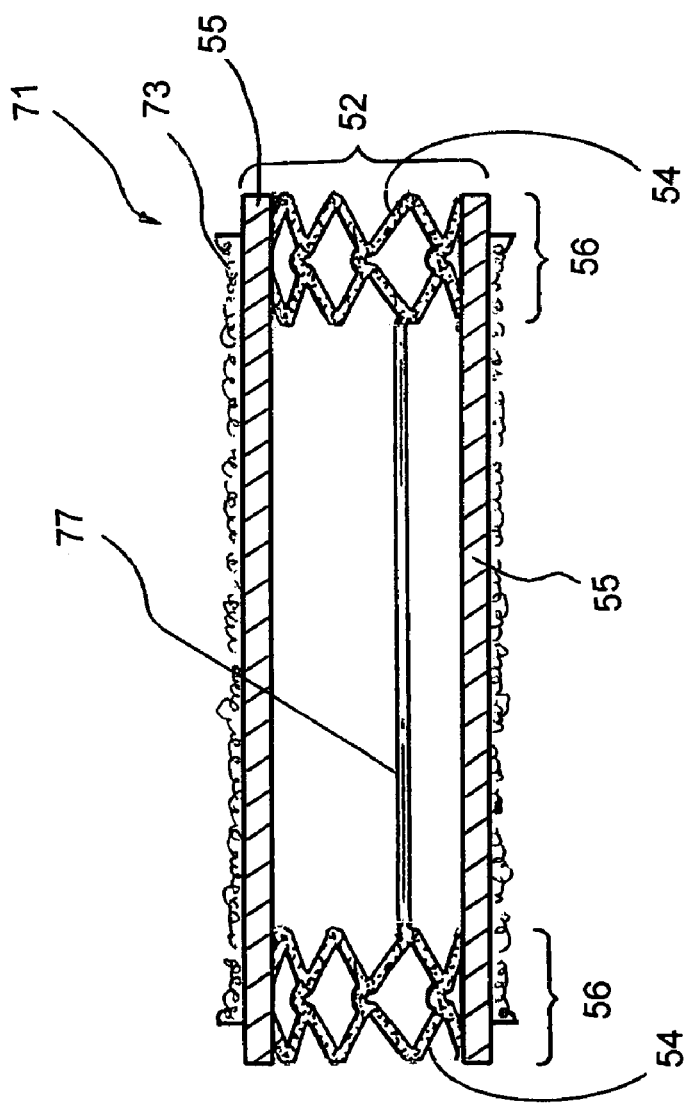
FIG. 8A is another illustrative example of a composite vascular graft with an endoluminal support element and end retaining-elements.

FIG. 8A shows another illustrative example of a composite vascular graft with an endoluminal support element having end retaining-elements 54, while FIG. 8B shows an end cross-sectional view of the composite vascular graft in FIG. 8A. In some aspect, a second composite vascular graft 71 has at least one site-specific angiogenesis factor for enhanced angiogenesis comprising a supported vascular graft 52, and a substrate 73 coated onto the supported vascular graft 52, wherein the substrate 73 is selected from the group consisting of collagen, heparinized collagen, crosslinked collagen, and crosslinked heparinized collagen, and wherein the substrate is incorporated with the at least one angiogenesis factor. The supported graft 52 further comprises two end retaining-elements 54 and an endoluminal support 77 securely coupled to the end retaining-elements 54, wherein each of the end retaining-elements 54 is secured to the respective end section 56 of the vascular graft 55 by suturing, stitching, welding or gluing techniques. In one aspect, the end retaining-element 54 is an expandable support to radially extend the end section 56 of the vascular graft 52 firmly against the vessel wall of a native blood vessel when implanted percutaneously. The endoluminal support 77 which can be a straight, spiral or curved structure is to secure the two end retaining-elements 54 together at a collapsed state or at an expanded state of the composite supported vascular graft 71. The angiogenesis factor-loaded substrate 73 may cover fully or at least a portion of the outer portion of the supported vascular graft 52.

From the foregoing description, it should now be appreciated that a vascular graft having site-specific angiogenesis factors or antagonists and methods thereof has been disclosed. The vascular graft has site-specific angiogenesibility for enhancing peripheral revascularization or neovascularization for blood perfusion so as to save the diseased foot from amputation, in one example. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A method for enhancing coronary collateral development of a diabetic patient comprising implanting a composite supported vascular graft, wherein said composite supported vascular graft comprises at least one angiogenesis factor effective for enhancing the coronary collateral development of the patient site-specifically.

2. The method according to claim 1, wherein the step of implanting is carried out by a percutaneous delivery apparatus, the composite supported vascular graft being collapsibly inserted within said delivery apparatus during a graft delivery phase.

3. The method according to claim 1, wherein the supported graft comprises a biological or synthetic tubular conduit having a first end, a second end, and at least one end retaining-element, the at least one end retaining-element being sized and configured for stabilizing said first end of the biological or synthetic tubular conduit in place after implantation.

4. The method according to claim 3, wherein the step of stabilizing is carried out by expanding the end retaining-element radially outwardly.

5. The method according to claim 1, wherein the supported graft comprises a synthetic tubular porous member having at least one retaining-element, the at least one retaining-element being sized and configured for stabilizing said tubular member in place after implantation.

6. The method according to claim 5, wherein the step of stabilizing is carried out by expanding the at least one retaining-element radially outwardly.

7. The method according to claim 1, wherein said at least one angiogenesis factor is VEGF (vascular endothelial growth factor).

8. The method according to claim 1, wherein said composite supported vascular graft comprises a supported tubular graft and a substrate coated onto said supported tubular graft, wherein said substrate comprises the at least one angiogenesis factor.

9. The method according to claim 8, wherein said substrate is collagen or heparinized collagen.

10. The method according to claim 8, wherein said substrate is crosslinked collagen or crosslinked heparinized collagen.

11. The method according to claim 8, wherein said substrate is blood clot or hydrogel.

12. The method according to claim 1, wherein said composite supported vascular graft comprises a tubular conduit wrapped onto and around said supported vascular graft and a substrate coated onto said supported tubular conduit, wherein said substrate comprises the at least one angiogenesis factor.

13. The method according to claim 12, wherein said substrate is collagen or heparinized collagen.

14. The method according to claim 12, wherein said substrate is crosslinked collagen or crosslinked heparinized collagen.

15. The method according to claim 12, wherein said substrate is blood clot or hydrogel.

16. The method according to claim 12, wherein said tubular conduit is a biological tubular conduit selected from the group consisting of internal mammary artery, umbilical vein, urethra, pericardium, jugular vein, genetically altered blood vessel, and combinations thereof.

17. The method according to claim 16, wherein said substrate is collagen or heparinized collagen.

18. The method according to claim 16, wherein said substrate is crosslinked collagen or crosslinked heparinized collagen.

19. The method according to claim 16, wherein said substrate is blood clot or hydrogel.

20. The method according to claim 12, wherein said tubular conduit is a synthetic tubular conduit made of polytetrafluoroethylene or polyester.

* * * * *